(12) United States Patent
Lilley et al.

(10) Patent No.: US 7,979,938 B2
(45) Date of Patent: Jul. 19, 2011

(54) CHANGING AMPLITUDE OF MOVEMENT BY CHANGING THE DRIVE FREQUENCY OF A TOOTHBRUSH BRUSHHEAD

(75) Inventors: Ronald C. Lilley, Federal Way, WA (US); Scott E. Hall, Issaquah, WA (US); John W. Pace, Bothell, WA (US); William E. Bryant, North Bend, WA (US); Joseph W. Grez, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 799 days.

(21) Appl. No.: 10/582,837

(22) PCT Filed: Dec. 9, 2004

(86) PCT No.: PCT/IB2004/052741
§ 371 (c)(1),
(2), (4) Date: Mar. 11, 2008

(87) PCT Pub. No.: WO2005/058188
PCT Pub. Date: Jun. 30, 2005

(65) Prior Publication Data
US 2008/0168611 A1    Jul. 17, 2008

Related U.S. Application Data

(60) Provisional application No. 60/529,597, filed on Dec. 15, 2003.

(51) Int. Cl.
*A61C 17/32* (2006.01)
*A61C 17/22* (2006.01)
*A61C 17/34* (2006.01)
*H02P 7/00* (2006.01)

(52) U.S. Cl. .......................................... 15/22.1; 310/10
(58) Field of Classification Search .................... 15/22.1
See application file for complete search history.

(56) References Cited

U.S. PATENT DOCUMENTS

| | | | |
|---|---|---|---|
| 4,403,176 A | | 9/1983 | Cranston |
| 5,189,751 A | | 3/1993 | Giuliani et al. |
| 5,613,259 A | | 3/1997 | Craft et al. |
| 5,784,742 A | * | 7/1998 | Giuliani et al. ............... 15/22.1 |
| 6,002,195 A | * | 12/1999 | Puskas ........................ 310/325 |
| 6,664,748 B2 | * | 12/2003 | Kushida et al. ............... 318/139 |
| 6,918,300 B2 | * | 7/2005 | Grez et al. ...................... 73/579 |
| 2002/0084707 A1 | | 7/2002 | Tang |
| 2002/0156402 A1 | * | 10/2002 | Woog et al. ..................... 601/46 |

FOREIGN PATENT DOCUMENTS

| | | |
|---|---|---|
| EP | 0435329 A2 | 7/1991 |
| EP | 0454188 A2 | 10/1991 |
| EP | 0625017 B1 | 5/2000 |
| GB | 2356311 A | 5/2001 |

(Continued)

*Primary Examiner* — Monica S Carter
*Assistant Examiner* — Stephanie Newton
(74) *Attorney, Agent, or Firm* — Paul Im

(57) ABSTRACT

The drive system drives a brushhead at a driving frequency. The drive system includes a frequency modulation system which changes the driving frequency about a center frequency in such a manner, with selected frequency deviation and modulation frequency, which interacts with the resonance of the brushhead to produce a change of amplitude in the movement of the brushhead within a range of 5-30%.

13 Claims, 5 Drawing Sheets

FOREIGN PATENT DOCUMENTS

| | | |
|---|---|---|
| JP | 3243529 | 10/1991 |
| JP | 6510675 | 12/1994 |
| JP | 2001314235 | 11/2001 |
| JP | 2002239458 | 2/2002 |
| JP | 2003153741 | 5/2003 |
| JP | 3472871 | 9/2003 |
| WO | 9216160 | 10/1992 |
| WO | 9533419 | 12/1995 |

\* cited by examiner

CHANGING AMPLITUDE OF MOVEMENT BY CHANGING THE DRIVE FREQUENCY OF A TOOTHBRUSH BRUSHHEAD

CROSS REFERENCE TO RELATED APPLICATION

This application claims the benefit of U.S. provisional application Ser. No. 60/529,597 filed Dec. 15, 2003, which is incorporated herein whole by reference.

This invention relates generally to power toothbrushes, and more specifically concerns such a toothbrush which is driven in a manner to produce a periodic change or variation in amplitude of a brushhead portion (which includes the bristles and bristle plate) of the toothbrush during operation thereof.

In power toothbrushes, there is usually a correlation between the amplitude of brushhead movement as it oscillates, relative to both cleaning effectiveness and sensory experience. Greater amplitude provides better cleaning results. However, there is a practical upper limit to the amplitude, above which discomfort occurs to the average user, although there is uncertainty as to the particular characteristics of the amplitude which are responsible for the discomfort. In the present invention, the amplitude is varied in a particular manner, allowing a user to tolerate more amplitude, which increases the sensory brushing experience and improves the cleansing effect of the toothbrush as well.

Accordingly, the present invention is a system for resonantly driving a power toothbrush having a resonant frequency, wherein a brushhead portion of the toothbrush moves in operation through a path with an amplitude about a center point, comprising: a resonant drive system for driving a brushhead at a drive frequency, the drive system including a circuit for changing the drive frequency relative to the center frequency to produce a periodic change of amplitude of the brushhead portion within the range of 5-30%, providing an improved sensory experience without discomfort to the user.

BEST MODE FOR CARRYING OUT THE INVENTION

Typically, power toothbrushes having a brushhead portion designed to oscillate about a center position are driven at a preselected frequency, referred to herein as a center frequency $F_C$. The center frequency is determined by the designer of the drive system and may be selected to be at or near the resonant frequency of the toothbrush to provide maximum efficiency relative to power consumed by the toothbrush during operation.

An example of such a toothbrush, using an electromagnetic drive system, is shown in U.S. Pat. No. 5,189,751, which is owned by the assignee of present invention, the contents of which are hereby incorporated by reference. However, it should be understood that the present invention is not limited to a particular drive system, such as that shown in the '751 patent. Many other drive systems which produce an oscillating brushhead action are well known and can be used with the present invention.

Figure 1:
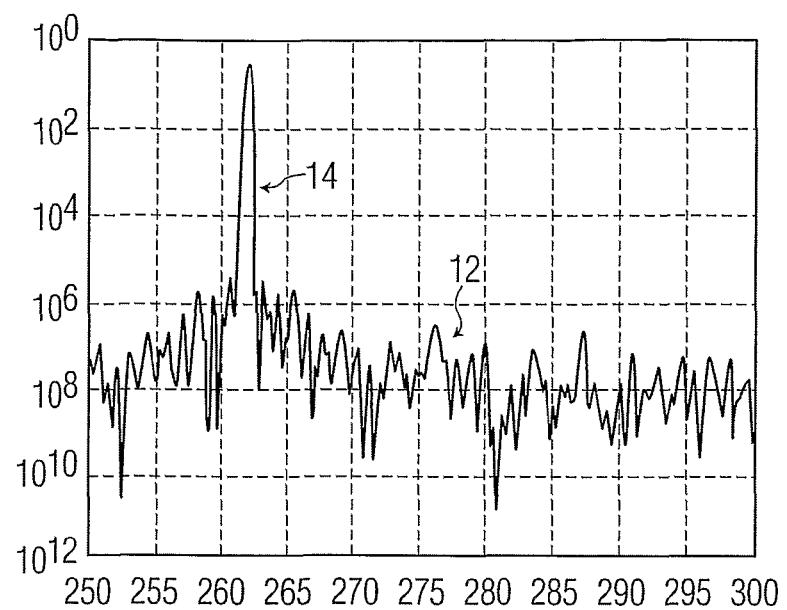
FIG. 1 is a diagram of brushhead voltage (energy) against frequency for a power toothbrush having a known resonant frequency at approximately 259 Hz.

Typically, a resonant drive toothbrush will operate slightly off resonance, since at resonance the amplitude of brushhead movement is quite high, resulting in significant discomfort to the average user. When the toothbrush is operated slightly off resonance, by 3 or 4 Hz, for instance, either above or below the resonant frequency, efficient cleaning results are obtained without discomfort to the user. FIG. 1 shows a plot of brushhead voltage (energy) against frequency for a resonant drive toothbrush. Note that the plot line 12 has one large peak at region 14, in the vicinity of the resonant frequency of the toothbrush.

As indicated above, it is known that amplitude of the toothbrush brushhead movement during its oscillation is a major factor in cleaning of the teeth, as well as providing the desired sensory effect of cleaning produced by action of the toothbrush. The sensory effect is quite important, as it provides the user an experience which indicates that an effective cleaning of the teeth and treatment of the gums has in fact occurred. Increasing amplitude thus would appear to be desirable, to increase cleaning and sensory effect, but as indicated above, increasing amplitude beyond a particular point will result in significant discomfort to the average user.

In the present invention, the drive frequency is changed periodically, about $F_C$, such as by frequency modulation, to produce a periodic change ($\Delta$) in motion (amplitude) of the brushhead, producing in effect an amplitude (motion) modulation, which results in an increase in average amplitude of brush movement. This produces an improved sensory brushing experience for the user, as well as a possible improvement in cleaning effect, without discomfort to the user.

In the present invention, with a resonant drive toothbrush, the center frequency $F_C$ is first moved closer to the resonant frequency of the toothbrush, typically closer than would be done otherwise (because of resulting discomfort). The closeness of the center frequency to the resonant frequency has a significant effect on the resulting change of amplitude of brush movement due to frequency modulation. In the embodiment shown, for instance, for a toothbrush resonant frequency of 256.5, the center frequency is 259 Hz.

Figure 4:
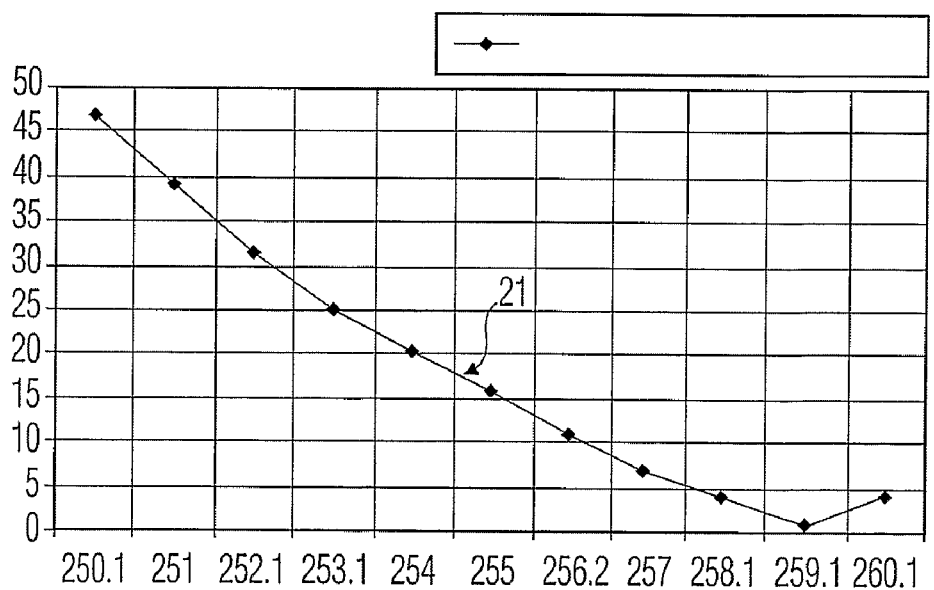
FIGS. 4 and 5 show diagrams of change (variation) of amplitude and peak amplitude against brushhead resonant frequency for a power toothbrush driven at 259 Hz.
Figure 5:
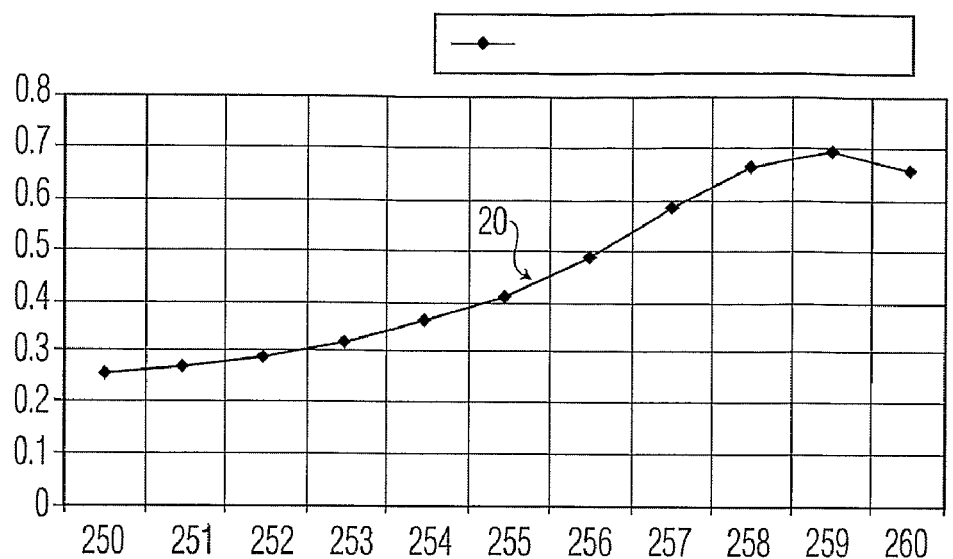

As the center frequency approaches the resonant frequency, the peak amplitude approaches its highest point, while the change or variation in $\Delta$ amplitude approaches a minimum. This is shown graphically in FIGS. 4 and 5, with plots of peak amplitude (20) and change in amplitude (21) against resonant frequency for a toothbrush driven at a frequency of 259 Hz with frequency modulation. Factors in the drive signal which affect the amplitude change of the brushhead include the frequency deviation (D) about $F_C$, i.e. the plus and minus variation of the drive frequency relative to the center frequency, the modulation frequency ($F_M$), the wave shape (all illustrated in FIG. 10 (which is a plot of frequency against time) and the duty factor.

Figure 9:
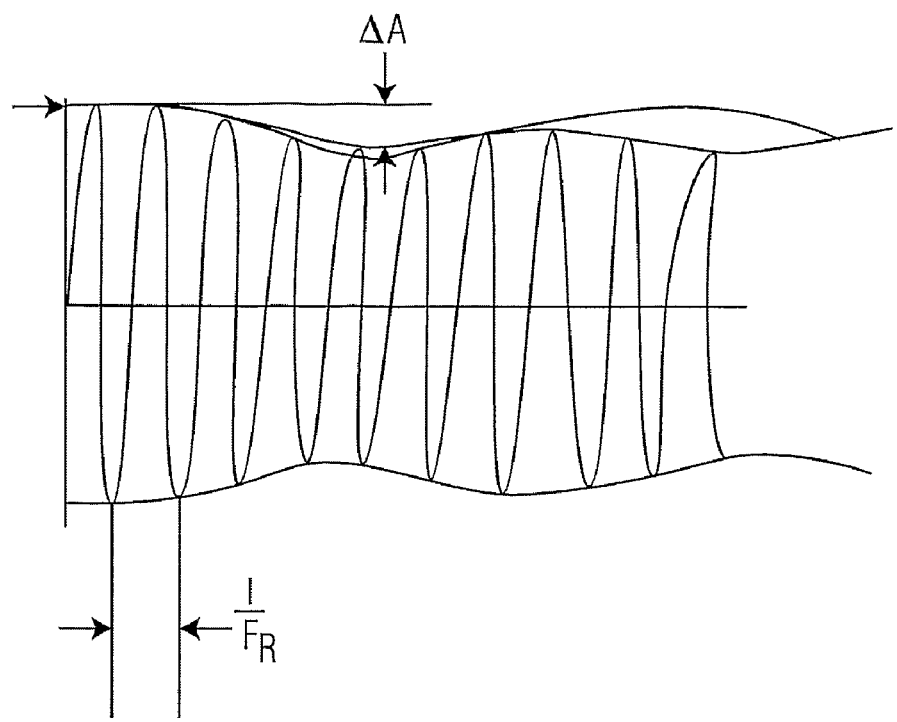
FIGS. 9 and 10 are diagrams of variations in amplitude of the brush portion of the toothbrush against time and variation in drive frequency against time, respectively.

The combination of the above frequency modulation factors (in particular the modulation frequency ($F_m$), the frequency deviation (D) and the wave shape must maintain the change of amplitude within a range of 5-30%. A change (variation) in amplitude is illustrated in FIG. 9, which is a plot of brushhead amplitude variation against time for a frequency modulated drive signal about $F_C$. Below 5% there is effectively no change in the sensory brushing experience or cleaning, while above 30% there is significant discomfort to the average user. Preferably, the change is not greater than 20%, and most preferably is 10%.

Figure 10:
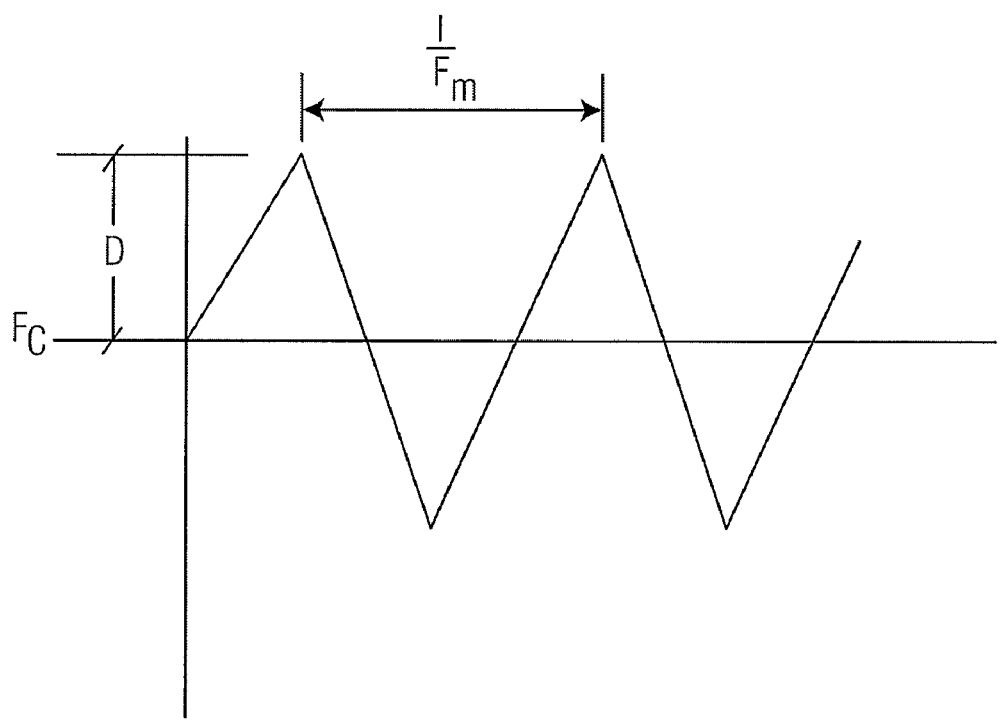

The wave shape refers to the manner in which the drive frequency is changed, i.e. changing the drive frequency in one step is a square wave modulation signal, while changing the frequency in a series of smaller steps over time to reach the maximum deviation is a triangular wave modulation signal, such as shown in FIG. 10.

As indicated above, the peak amplitude of brushhead motion is the greatest when $F_C$ is at the resonant frequency, while change (variation) in amplitude is at a minimum when $F_C$ is at the resonant frequency. Hence, as indicated above, to obtain a periodic change of amplitude, which is the thrust of the present invention, the center frequency must be some amount away from the resonant frequency of the device, in the present embodiment, approximately 3 Hz.

While the factors discussed herein influencing change of amplitude for frequency modulation of the drive signal are based on a resonant drive system, it is quite possible that another type of modulation of the drive signal, resulting in a periodic change of amplitude, will also enhance cleaning effects and/or the sensory/brushing experience of cleaning in non-resonant systems as well. However, the explanation herein is based on a resonant drive system.

Figure 6:
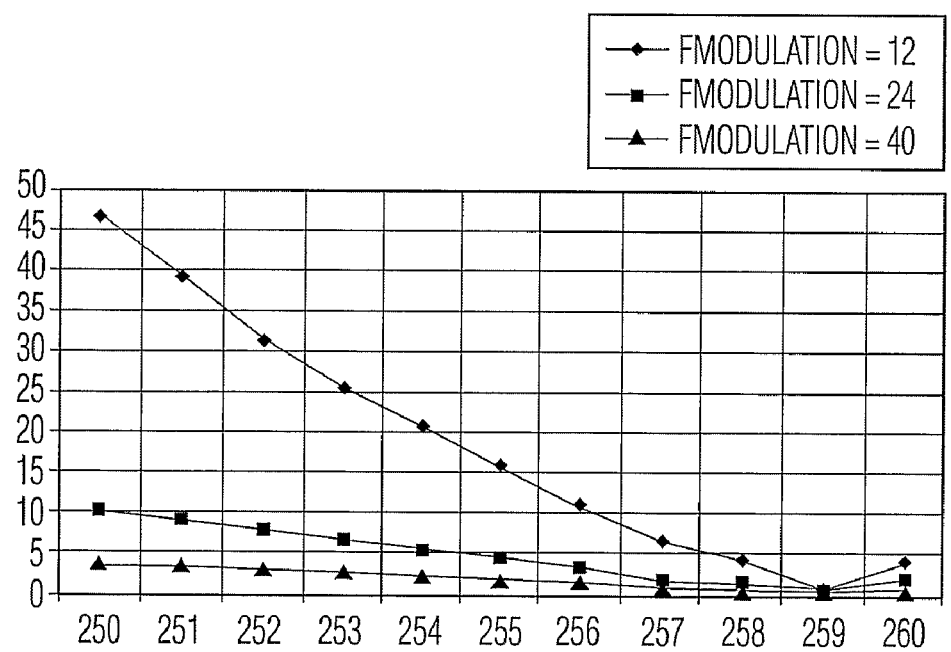
FIGS. 6 and 7 show diagrams of change (variation) in amplitude against brushhead resonant frequency for a frequency modulated drive signal with different modulation rate (FIG. 6) and different maximum frequency deviations of the modulation (FIG. 7).
Figure 7:
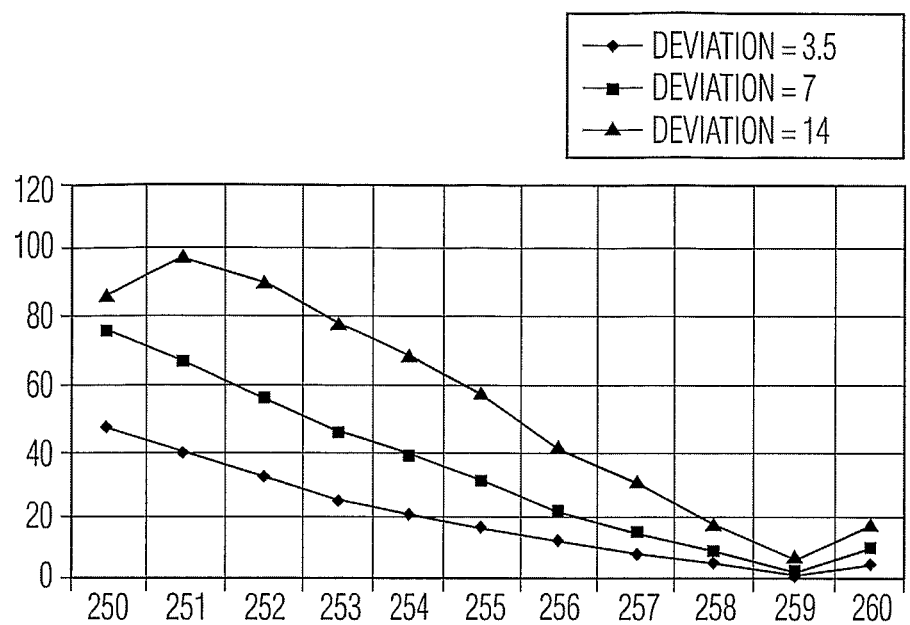

The effects of different modulation frequencies (rates) and different frequency deviations (D) are shown in the graphs of FIGS. 6 and 7. Both of these graphs plot change of amplitude (Δ amplitude) versus brushhead resonant frequency for a toothbrush with a center frequency $F_C$ of 259 Hz. FIG. 6 shows that an increase in modulation frequency results in a significant decrease in change of brush amplitude (Δ amplitude), while FIG. 7 shows that an increase in frequency deviation results in an increase in change of brush amplitude (Δ amplitude) for a selected frequency difference between resonant frequency and center frequency (see for instance a resonant frequency of 256.5 with the center frequency of 259 Hz).

More particularly, from FIG. 6, for a given center frequency $F_C$, the modulation frequency has a strong inverse effect on amplitude modulation. For instance, in an embodiment where the center frequency is 259 Hz, relative to a resonant frequency of 256.5 Hz, a 12 Hz modulation frequency produces a change of amplitude within a particular range, depending upon the other factors of frequency deviation, wave shape and duty factor. Increasing the modulation frequency from 12 Hz to 24 Hz reduces the change (variation) in amplitude or ΔA substantially, and further increasing the modulation frequency to 40 Hz brings the amplitude variation close to zero.

More particularly, from FIG. 7, deviation (D), the change in frequency relative to the center frequency $F_C$, has a direct effect on the amplitude modulation. For instance, in the embodiment shown, the preferred deviation is ±3.5 Hz. Doubling the deviation approximately doubles the change (variation) of amplitude.

Other factors influencing to some extent change of amplitude, as indicated above, include the wave shape of the modulation signal and the duty factor of the modulating frequency. The use of a triangle wave shape for the change in modulating frequency as opposed to a square wave shape, has approximately half the effect on change of amplitude (ΔA). With respect to the duty factor, the change in amplitude increases when the duty factor is reduced.

Figure 3:
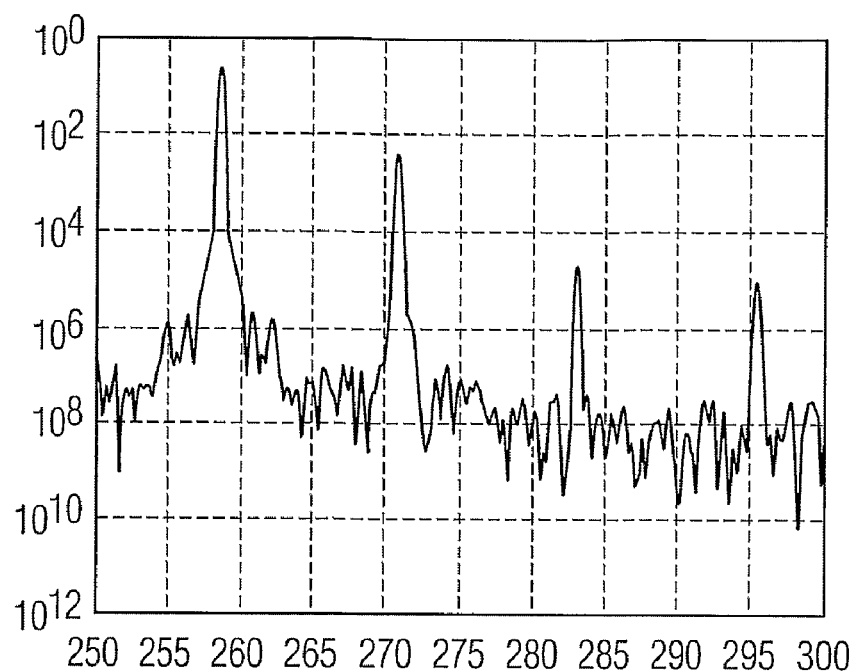
FIG. 3 is a diagram of brushhead voltage (energy) against frequency using the system of FIG. 2.

The preferred embodiment, for an amplitude change (ΔA) around 10%, has a resonant frequency of 262 Hz, a center frequency $F_C$ of 259 Hz, a modulation frequency $F_M$ of 12 Hz and a frequency deviation (D) of 3.5 Hz. The wave shape is triangular and the duty factor 48%. With such a system, an increase in sensory experience occurs, as well as improved cleaning, without discomfort. FIG. 3 shows the distribution of energy relative to frequency for such an arrangement, specifically the drive signal's frequency spectrum.

Figure 2:
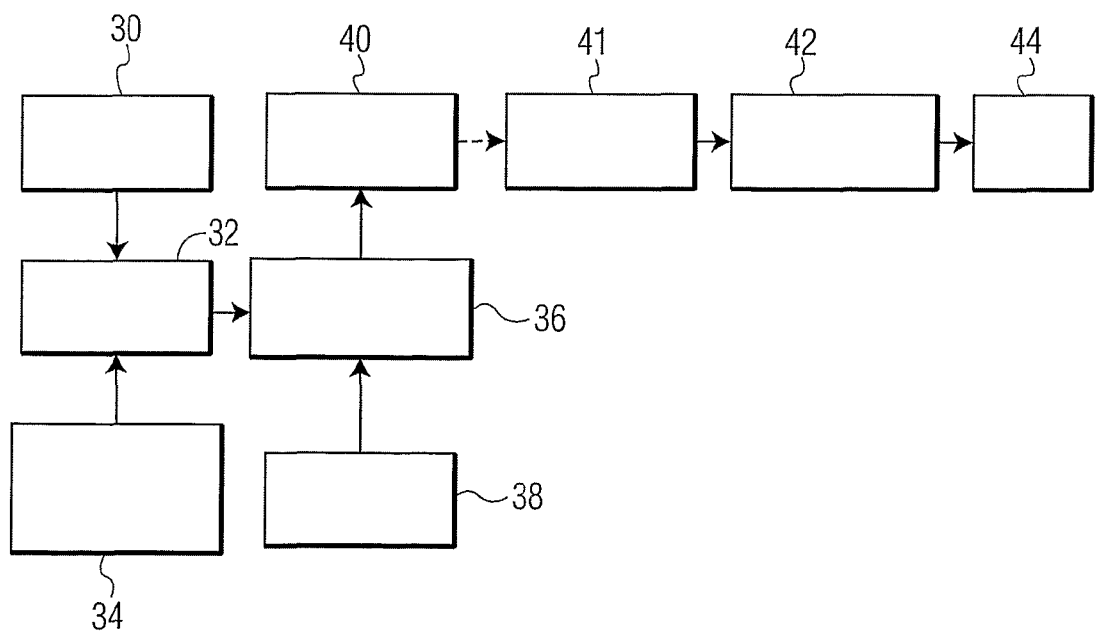
FIG. 2 is a block diagram of one embodiment of the toothbrush drive system of the present invention.

FIG. 2 is a block diagram showing the structural implementation of the system described above. A center frequency $F_C$ is produced by a circuit, block 30. The center frequency is applied to a frequency source circuit 32, to which is also supplied the frequency modulation signal $F_M$ by block 34. The frequency generated by the frequency source 32 is applied to the drive electronics of the toothbrush, as represented by block 36, which is in turn driven by a power source 38, such as a battery.

In one embodiment, the drive electronics 36 drives a magnetic drive coil 40, the action of which is coupled by a magnetic coupling arrangement 41 to a mechanical resonant system 42, which in turn drives the brush 44 in an oscillating manner.

Figure 8:
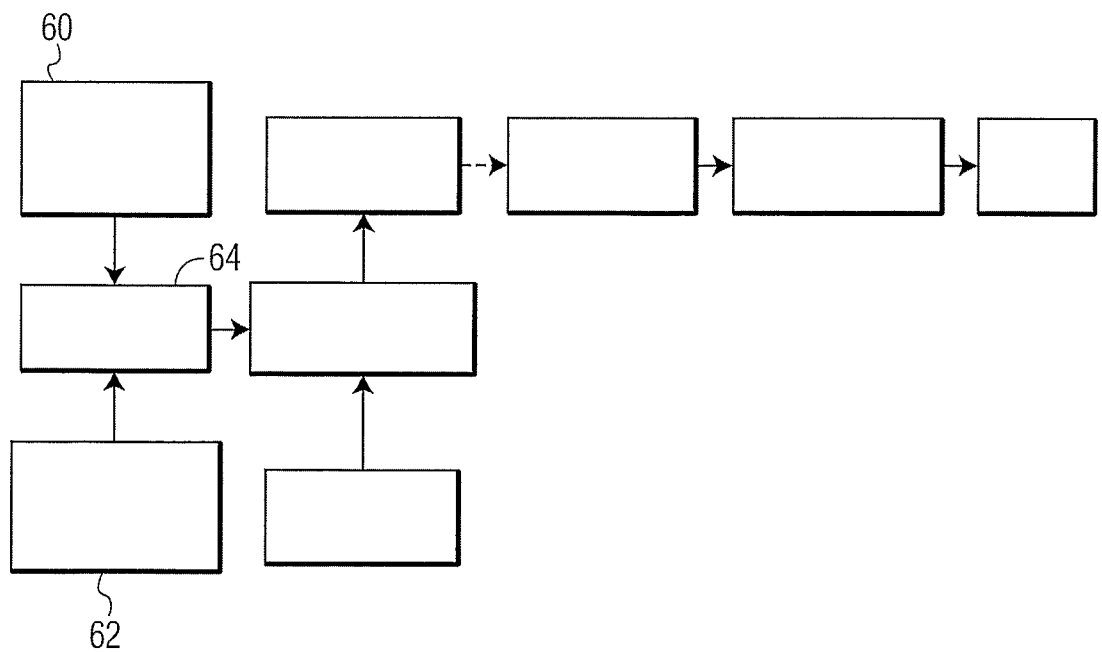
FIG. 8 is a block diagram of another embodiment of the present invention.

In the arrangement above, the change of drive frequency about the center frequency $F_C$ is accomplished by conventional frequency modulation means, which are well known, in which the drive frequency is changed at a selected rate. However, the change of frequency could be accomplished by another arrangement. This arrangement is shown in FIG. 8. Two simultaneously generated drive signals are combined together, with the resulting signal driving the brushhead. A first frequency signal is generated by frequency generator 60, while a second frequency signal is generated by frequency generator 62. Typically, one signal will be at the resonant frequency of the device, while the other signal will be a frequency somewhat removed from the resonant frequency. In one case, for a resonant frequency of 262 Hz (the first frequency), the second frequency could be 242 Hz. Generally, the difference will be in the range of 5-30 Hz.

The two signals are then applied to an op-amp 64, where they are combined. The output of the op-amp 64 is a combined signal, the result of the two signals being "beat", which produces a change in brushhead amplitude. The output is filtered to remove high frequencies. The remainder of the drive circuit shown in FIG. 8 is similar to that of FIG. 2.

Again, however, there are limitations relative to the range of change of amplitude over time, i.e. amplitude modulation, because of user discomfort. The selection of the frequencies of the two signals is thus an important factor relative to achieving the desired results.

As mentioned above, the first embodiment, using frequency modulation, is described above in a resonant drive system, as is the other embodiment, with one of the two signals being at the resonant frequency.

Hence, a system has been disclosed for producing a change in amplitude, in effect an amplitude modulation, of the brushhead movement by frequency modulating the drive signal. The amplitude modulation results in an improved sensory experience for the user and improved cleaning effect without discomfort.

Although a preferred embodiment of the invention has been disclosed for purposes of illustration, it should be understood that various changes, modifications and substitutions may be incorporated in the embodiment without departing from the spirit of the invention which is defined by the claims as follows:

The invention claimed is:

1. A system for resonantly driving a power toothbrush having a resonant frequency, wherein a brushhead portion of the toothbrush moves in operation through a path with an amplitude about a center point, comprising:
   a resonant drive system for driving a brushhead at a drive frequency, the drive system including a circuit for changing the drive frequency to produce a predetermined regularly varying drive frequency relative to a center frequency to produce a regularly varying amplitude of the brushhead portion within the range of 5-30%, providing an improved sensory experience without discomfort to the user.

2. The system of claim 1, wherein the change of amplitude is less than 20%.

3. The system of claim 1, wherein the center frequency is different from the resonant frequency of the toothbrush within a range of 0 to 5 Hz.

4. The system of claim 3, wherein the changing of the drive frequency is accomplished by frequency modulation.

5. The system of claim 4, wherein the difference between the center frequency and the resonant frequency is approximately ±3 Hz.

6. A system of claim 1, wherein the driving frequency has a frequency deviation with a range of 1-14 Hz from the center frequency.

7. The system of claim 6, wherein the frequency deviation is approximately 3.5 Hz.

8. The system of claim 1, wherein the driving frequency change has a modulation frequency within the range of 3-40 Hz.

9. The system of claim 8, wherein the modulation frequency is approximately 12 Hz.

10. The system of claim 4, wherein the change of the drive frequency is in the form of a triangular wave.

11. The system of claim 1, wherein the change of drive frequency has a duty factor of approximately 48%.

12. The system of claim 1, wherein the drive system includes two driving signal sources, one signal source being at approximately the resonant frequency and the other signal source being at a frequency which is slightly different than the resonant frequency.

13. The system of claim 12, wherein the frequency of the second signal source is different than the frequency of the first source within a range of 5 to 30 Hz.

* * * * *